(12) United States Patent
Xu et al.

(10) Patent No.: US 9,681,844 B2
(45) Date of Patent: Jun. 20, 2017

(54) BIOPOTENTIAL SIGNAL ACQUISITION SYSTEM AND METHOD

(71) Applicants: IMEC VZW, Leuven (BE); Stichting IMEC Nederland, Eindhoven (NL)

(72) Inventors: Jiawei Xu, Eindhoven (NL); Refet Firat Yazicioglu, Leuven (BE)

(73) Assignees: IMEC VZW, Leuven (BE); Stichting IMEC Nederland, Eindhoven (NL)

( * ) Notice: Subject to any disclaimer, the term of this patent is extended or adjusted under 35 U.S.C. 154(b) by 553 days.

(21) Appl. No.: 14/315,520

(22) Filed: Jun. 26, 2014

(65) Prior Publication Data

US 2015/0005585 A1  Jan. 1, 2015

(30) Foreign Application Priority Data

Jun. 27, 2013  (EP) .................................... 13173917

(51) Int. Cl.
*A61B 5/00* (2006.01)
*A61B 5/04* (2006.01)
(Continued)

(52) U.S. Cl.
CPC .......... *A61B 5/7207* (2013.01); *A61B 5/0402* (2013.01); *A61B 5/04004* (2013.01);
(Continued)

(58) Field of Classification Search
CPC ......... A61B 5/04–5/0496; A61B 5/72–5/7225; H03F 3/45484; H03F 3/45488; H03F 3/45928–3/45995; A61N 1/00–1/08
See application file for complete search history.

(56) References Cited

U.S. PATENT DOCUMENTS

| 5,792,063 A * | 8/1998 | Danielsson .......... A61B 5/0424 600/509 |
| 2004/0010289 A1* | 1/2004 | Biggs ....................... A61N 1/06 607/2 |

(Continued)

OTHER PUBLICATIONS

European Search Report, European Patent Application 13173917.9, dated Dec. 3, 2013.
(Continued)

*Primary Examiner* — Huy Q Phan
*Assistant Examiner* — David Frederiksen
(74) *Attorney, Agent, or Firm* — McDonnell Boehnen Hulbert & Berghoff LLP

(57) ABSTRACT

A biopotential signal acquisition system, comprising: a first active electrode including an integrated pre-amplifier and an analogue to digital converter; a second active electrode including an integrated pre-amplifier and an analogue to digital converter, wherein the second active electrode has variable gain; a test signal generator for generating a test signal at a test frequency and coupling the test signal to the first and/or second active electrodes; and a digital signal processor configured to: process the digital outputs of the first and second active electrodes to derive a gain control signal based on a difference between the first and second active electrode outputs at the test frequency, and apply the gain control signal to the second active electrode. The disclosure also relates to an electronic circuit or device and a biopotential signal acquisition method.

16 Claims, 10 Drawing Sheets

(51) Int. Cl.

| | |
|---|---|
| *A61B 5/0402* | (2006.01) |
| *A61B 5/0428* | (2006.01) |
| *A61B 5/0476* | (2006.01) |
| *A61B 5/0488* | (2006.01) |
| *A61B 5/0496* | (2006.01) |
| *A61B 5/0408* | (2006.01) |
| *A61B 5/0478* | (2006.01) |
| *A61B 5/0492* | (2006.01) |

(52) U.S. Cl.
CPC .......... *A61B 5/0408* (2013.01); *A61B 5/0428* (2013.01); *A61B 5/0476* (2013.01); *A61B 5/0478* (2013.01); *A61B 5/0488* (2013.01); *A61B 5/0492* (2013.01); *A61B 5/0496* (2013.01); *A61B 2562/0209* (2013.01)

(56) References Cited

U.S. PATENT DOCUMENTS

| | | | |
|---|---|---|---|
| 2005/0113703 A1* | 5/2005 | Farringdon | A61B 5/0428 600/509 |
| 2005/0215916 A1 | 9/2005 | Fadem et al. | |
| 2012/0071950 A1* | 3/2012 | Archer | A61N 1/36157 607/66 |
| 2014/0142447 A1* | 5/2014 | Takahashi | H03F 3/45475 600/509 |
| 2014/0247058 A1* | 9/2014 | Mortara | A61B 5/0424 324/601 |

OTHER PUBLICATIONS

Degen, Thomas et al., "Enhancing Interference Rejection of Preamplified Electrodes by Automated Gain Adaption", IEEE Transactions on Biomedical Engineering, vol. 51, No. 11, Nov. 1, 2004, pp. 2031-2039.

Degen, Thomas et al., "A Pseudodifferential Amplifier for Bioelectric Events With DC-Offset Compenstation Using Two-Wired Amplifying Electrodes", IEEE Transactions on Biomedical Engineering, vol. 53, No. 2, Feb. 1, 2006, pp. 300-310.

Farahani, Bahar Jalali, "Adaptive Digital Calibration Techniques for High Speed, High Resolution Sigma Delta ADCS For Broadband Wireless Applications", Dissertation, Presented in Partial Fulfillment of the Requirements for the Degree Doctor of Philosophy in the Graduate School of The Ohio State University, 2005, 207 pages.

* cited by examiner

Figure 1 – Prior Art

BIOPOTENTIAL SIGNAL ACQUISITION SYSTEM AND METHOD

CROSS-REFERENCE TO RELATED APPLICATION

This application claims priority to European Patent Application No. 13173917.9 filed on Jun. 27, 2013, the contents of which are hereby incorporated by reference.

FIELD OF THE DISCLOSURE

This disclosure relates to the acquisition of biopotential signals, such as, for example, ECG (electrocardiography), EEG (electroencephalography) or EMG (electromyography) signals.

BACKGROUND OF THE DISCLOSURE

Biopotentials are usually recorded using electrodes attached to the body, such as wet (gel) electrodes, or dry electrodes. The electrodes are used to measure biopotentials, which typically have a magnitude in the range of about 1 μV to 10 mV.

Active electrodes have been employed in biopotential acquisition systems, in which the electrodes are integrated with amplifiers for the suppression of interference picked up from cables. The active electrode based system is robust to cable motion artifacts and interferences, which makes it suitable for dry electrode applications.

In one example, an active electrode includes a passive electrode and a pre-amplifier that are integrated within the same package or board, which can be placed very close to the skin to extract the low-level biopotential signals. In this way, the signal path length between the electrode and the pre-amplifier may be minimized, maintaining the highest possible input impedance of the amplifier and lowest possible noise pick-up from electromagnetic fields. Furthermore, the output of the active electrode forms a low-impedance node and the interference and motion artifacts obtained by cable movement and electromagnetic fields in the vicinity can both be reduced when compared to a conventional passive electrode interface.

FIG. 1 shows the basic active electrode system. A reference active electrode 10 comprises an amplifier 12 and an analogue to digital converter 14. A first signal active electrode 16 comprises an amplifier 18 and an analogue to digital converter 20. The gain of the reference active electrode amplifier is shown as A and the gain of the signal active electrode amplifier is shown as A+ΔA. Thus, there may be a gain mismatch between the active electrodes.

Common mode interference is one of the problems in such active electrode biopotential signal acquisition systems. For example, biopotential signals can be affected by interference currents derived from the mains power supply lines, known as "common mode aggressors". The mains frequency generally falls within the frequency range of interest of biomedical signals, which makes such common mode signals a particular problem. For example, an ECG signal has its main frequency components in the range 0.5 Hz to 40 Hz, but signal information up to around 100 Hz or even 200 Hz is desired.

The common mode interference is represented by the signal source 22 in FIG. 1.

The interference signals can have larger amplitudes than the biopotential signals that are to be measured. This causes the biopotential amplifier to have very high common mode rejection ratio (CMRR) in order to eliminate the common mode interference signals appearing at the output of the amplifier, and thereby reject the 50 Hz or 60 Hz common mode interferences whilst extracting the biopotential signals.

One potential problem is that the common mode interference at the inputs of the active electrodes can be converted to a differential mode error at the outputs of active electrode pairs due to the voltage gain mismatch between the active electrode pairs, as well as the contact-impedance mismatch. The output error can have significant amplitude when compared to the amplitude of the biopotential signals. The CMRR of active electrode systems is usually limited by this voltage gain mismatch (VCM *ΔA) between the signal active electrode and the reference active electrode, which in return is due to the process variation and component mismatch.

The article "Enhancing Interference Rejection of Preamplified Electrodes by Automated Gain Adaptation" of Thomas Degen, in IEEE Transactions on Biomedical Engineering, Vol. 51, o. 11, November 2004, discloses adaptation of the gain of an analogue differential amplifier which follows the active electrodes in response to a detected amplified common mode signal. A common mode feedback system is also disclosed by which a common mode signal is fed back to the patient (for example via a driven right leg electrode).

SUMMARY OF THE DISCLOSURE

According to an embodiment of the disclosure, there is provided an improved biopotential signal acquisition system. According to an embodiment, there is provided a biopotential signal acquisition system comprising: a first active electrode including an integrated pre-amplifier and an analogue to digital converter; a second active electrode including an integrated pre-amplifier and an analogue to digital converter, wherein the second electrode has variable gain; a test signal generator for generating a test signal at a test frequency and coupling the test signal to the first and/or second electrodes; and a digital signal processor configured to process the digital outputs of the first and second active electrodes to derive a gain control signal based on a difference between the first and second electrode outputs at the test frequency, and apply the gain control signal to the second active electrode.

According to an embodiment, the disclosure provides a system in which active electrodes are used to provide digital outputs via internal ADCs. These digital signals are more robust to cable motion and interference than traditional analog outputs. A test common mode signal is used for CMRR calibration. This calibration involves adjusting the gain in the second active electrode, either by using a variable gain amplifier or implementing a variable gain in another component such as an analog to digital converter. The signal processing can be performed in the digital domain, which is generally more flexible and power/area efficient than in the analog domain.

In one implementation, the gain control signal is also digital, and the second active electrode then comprises a digital to analogue converter for deriving an analogue gain control signal.

According to an embodiment, the digital signal processor comprises a digital band pass filter tuned to the test frequency for producing the gain control signal. In this way, the response to the test frequency signal is extracted and used to derive the feedback control.

According to an embodiment, the test frequency is greater than 100 Hz and is not a multiple of 50 Hz or 60 Hz. In this way, the frequency of the test signal is above the biopotential signal bandwidth (for example 0.5 Hz-100 Hz), such that the test signal can be clearly differentiated from the biopotential signal and CMRR calibration can be performed during acquisition of the biopotential signal. Harmonics of the mains interference signals may also be avoided.

According to an embodiment, the test frequency is below 10 kHz. This avoids the need for very large bandwidth amplifiers.

The digital signal processor can comprise a digital low pass filter for removing the test signal frequency before providing the system output. Thus, the test frequency signal may not appear in the output provided by the signal acquisition system.

According to another embodiment, the system can comprise multiple active electrodes with variable gain. Thus, there can be at least a third active electrode comprising an integrated pre-amplifier and an analogue to digital converter, wherein the third active electrode has variable gain and is coupled to the test signal. The digital signal processor is then further configured to process the digital outputs of the first and third active electrode to derive a gain control signal based on a difference between the first and third active electrode outputs at the test frequency, and to apply the gain control signal to the third active electrode.

The first active electrode thus functions as a reference active electrode and is used for the derivation of the gain control signal of the other two (or more) active electrodes, which function as signal active electrodes.

Another embodiment further comprises a common mode feedback system. This can enable the test signal to be larger, without saturating the amplifiers. For a system with two electrodes, the outputs of the first and second active electrodes can be averaged to derive a combined signal representing the common mode signal at the output. This can then be used as a feedback control parameter. For a system with more electrodes, one functioning as reference electrode and the others functioning as signal electrodes, the outputs of the signal active electrodes can be averaged to derive a combined signal representing the common mode signal at the output.

In either case, a digital to analogue converter is provided for converting the combined signal into an analogue common mode feedback signal, which is provided to the active electrodes. An AC part of the common mode feedback signal can, for example, be subtracted from the input signal to the respective electrode, before amplification by the respective electrode pre-amplifier.

The disclosure also provides an electronic circuit or device comprising the biopotential signal acquisition system disclosed herein.

The disclosure also provides a biopotential signal acquisition method, comprising: capturing a first biopotential signal using a first active electrode including an integrated pre-amplifier and an analogue to digital converter; capturing a second biopotential signal using a second active electrode including an integrated pre-amplifier and an analogue to digital converter, the second active electrode having variable gain; generating a test signal at a test frequency and coupling the test signal to the first and/or second electrodes; and processing the digital outputs of the first and second active electrodes to derive a gain control signal based on a difference between the first and second active electrode outputs at the test frequency, and applying the gain control signal to the second electrode.

BRIEF DESCRIPTION OF THE DRAWINGS

Example embodiments of the disclosure will now be described with reference to the accompanying drawings, in which.

DETAILED DESCRIPTION

According to an embodiment, the disclosure provides an active electrode biopotential acquisition system in which the active electrodes provide digitized outputs. In the digital domain, a gain control signal is derived based on the response to a common mode test signal at a test frequency. This is fed back to one of the active electrodes and is used to adjust a gain of the active electrode. This provides a CMRR calibration system and method that can continuously adjust the voltage gain of an active electrode to compensate for the voltage gain difference between active electrodes and to improve CMRR during the biopotential signal acquisition.

Figure 2:
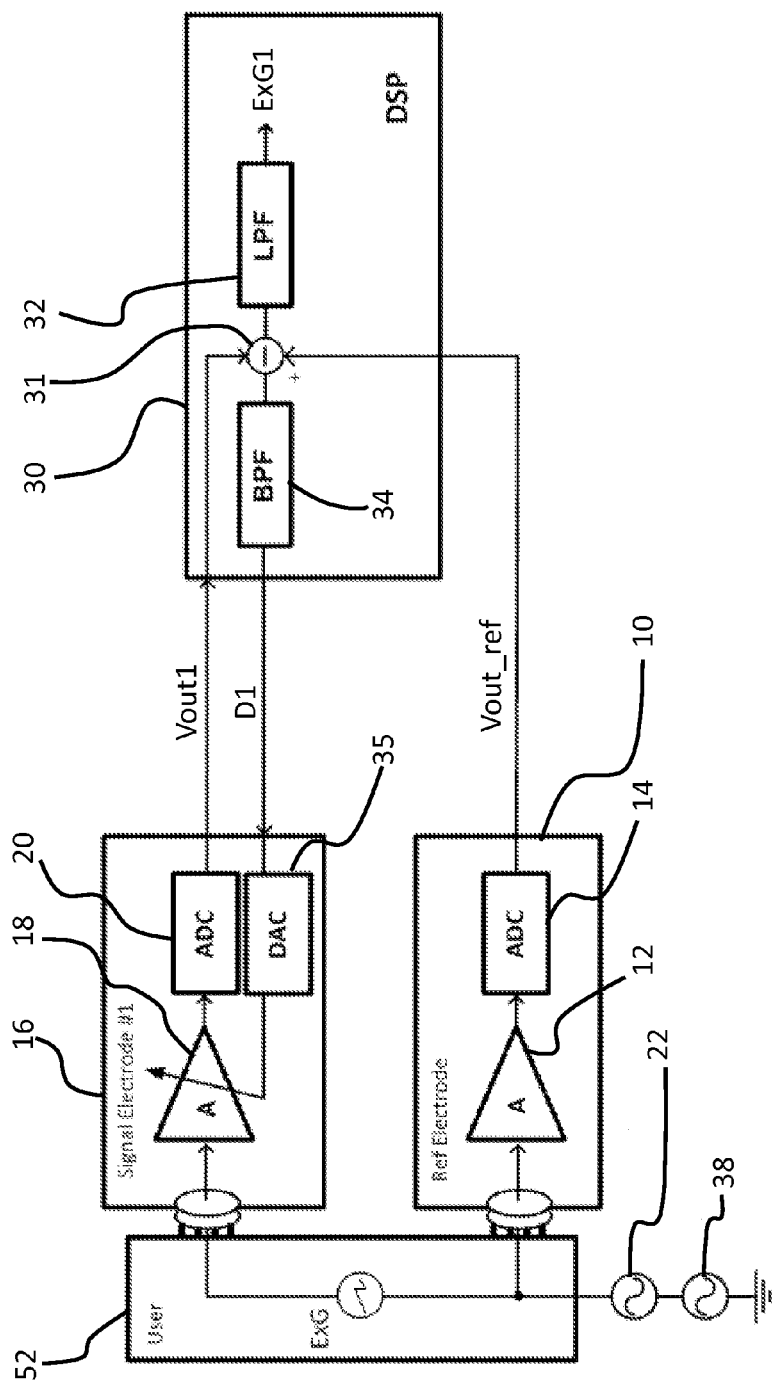
FIG. 2 shows a first embodiment of a signal acquisition system according to the disclosure.

FIG. 2 shows a first example of signal acquisition system of the disclosure.

Figure 1:
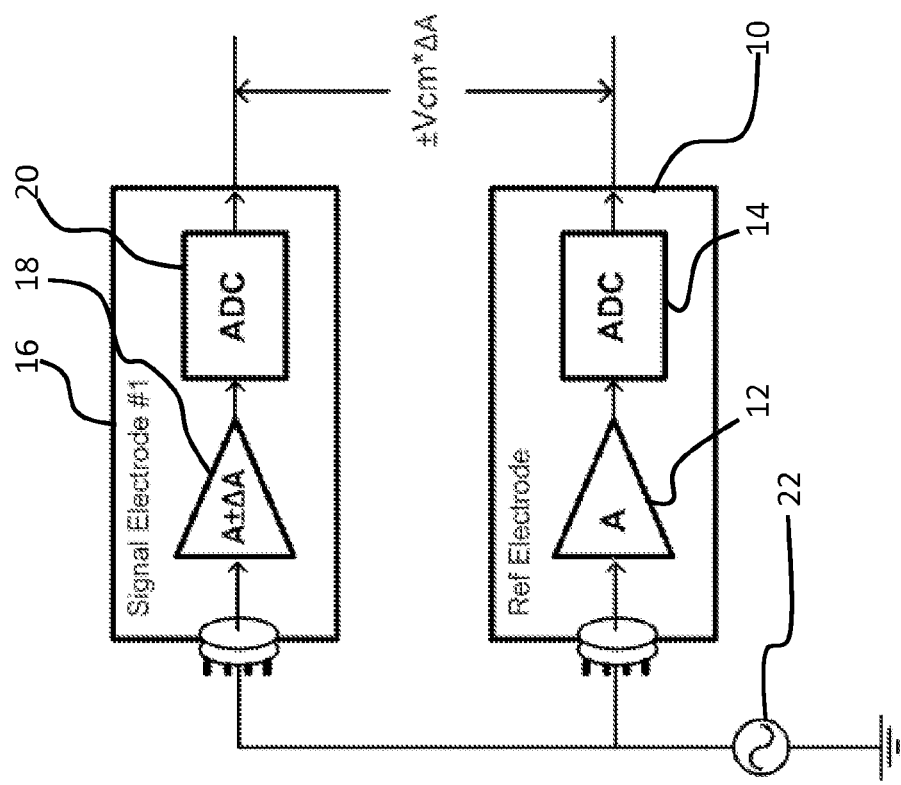
FIG. 1 shows schematically a known active electrode system for measuring biopotentials.

The same reference numbers are used as in FIG. 1 for the same or similar components. The ADC 20 of the signal active electrode 16 generates an output Vout1 and the ADC 14 of the reference active electrode 10 generates an output Vout_ref.

The reference active electrode 10 and the signal active electrode 16 provide their digital outputs to a digital signal processing unit 30. The active electrodes can include further analogue components that are not shown, such as filters and buffers.

A subtractor 31 generates a difference signal that provides the output of the system. This difference signal can be further amplified downstream, as required.

A test signal is generated by a signal generator 38 at a test frequency fCM. The test signal may be generated, for example, in the digital domain, and converted to an analogue signal by a digital to analogue converter.

The test signal can simply be a sine wave of a known amplitude, but more complex signals can also be used, such as a square wave or an input signal with a certain pattern. The use of a simple sine wave enables signal extraction with a simple bandpass filter as explained below.

The test signal is fed back to both active electrode inputs, as schematically represented by the signal source 38 in FIG. 2, in addition to the common mode interference signal represented by signal source 22.

This feedback can use a passive electrode (known as a "bias electrode"). This bias electrode is generally connected to a DC voltage source, and is used to bias the patient to certain DC voltage. The test signal can be superimposed on this DC voltage source, and the resulting signal is then coupled (indirectly) to the active electrodes via this bias electrode, which itself is coupled to the patient. Other alternative ways to couple the test signal to the active electrodes are discussed further below.

In an example, there is thus a DC bias with the test signal superimposed on the DC voltage that is sent to the passive bias electrode, and thus applied to the active electrodes via the user. In this way, the test signal passes through the patient, so that the CMRR calibration described below not only corrects gain mismatch from the active amplifiers, but also corrects for contact-impedance mismatch between the two active electrodes.

The test signal frequency may be above the frequency range of interest, for example, greater than 100 Hz, and may not be a harmonic of the mains frequency (50 Hz or 60 Hz).

In FIG. 2, the controller 30 has a low pass filter 32 to remove the test signal from the difference signal from the subtractor 31 before the output ExG1 is provided (where ExG indicates an EEG, ECG, EMG, or EOG signal, for example). A band pass filter 34 tuned to the test frequency is used for producing a digital gain control signal D1 for feedback to the signal active electrode 16.

The amplifier 18 of the signal active electrode 16 is a programmable gain amplifier with a controllable variable gain. This can be achieved with variable feedback resistors, for example, in conventional manner. The amplifier 12 can be the same amplifier as 18 but with fixed gain. They can, for example, be instrumentation amplifier circuits.

The signal active electrode 16 has a digital to analogue converter 35 for generating the analogue gain control signal, so that the gain can be tuned in order to reduce or cancel the difference between the electrode outputs to the common mode test signal, thereby tuning the amplifier gain for matching with the reference active electrode amplifier 12.

The gain calibration may be performed in the analogue domain, in the analogue amplifier 18.

Figure 9:
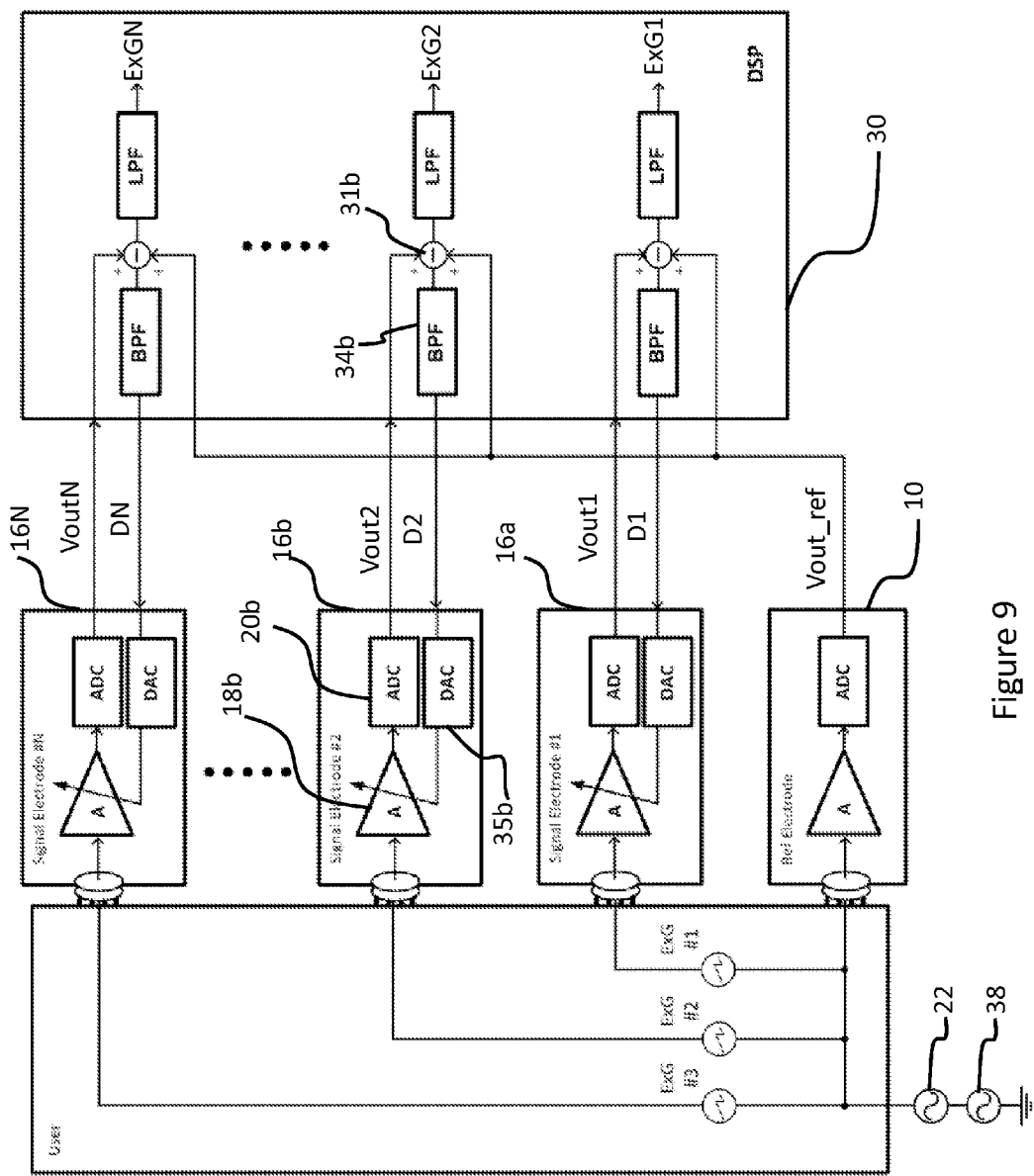
FIG. 9 shows how the system of FIG. 2 can be extended to have more than two active electrodes.

FIG. 2 shows one reference active electrode and one signal active electrode. However, the disclosure can be generalized for N active electrodes (as shown in FIG. 9). The calibration of the gain is carried out for N−1 signal active electrodes, with the other active electrode functioning as a reference for all the signal active electrodes.

The system of FIG. 2 is thus able to detect and compensate the gain mismatch (ΔA) and contact-impedance mismatch (ΔR) between the active electrodes, because the common-mode test signal is converted to a differential-mode signal between the outputs of the active electrodes due to their voltage gain mismatch. The feedback system adapts the voltage gain continuously to be equal to that of the reference active electrode 10.

In this arrangement, each active electrode provides digital outputs via the internal ADCs. Such digital signals are more robust to cable motion and interference than traditional analog outputs. The test common mode signal for CMRR calibration can be clearly differentiated by frequency selection from the biopotential signal (0.5 Hz-100 Hz). This means that the CMRR calibration can be performed during acquisition of the biopotential signal.

The active electrodes do not require any succeeding analog processor, since the gain calibration takes place in the active electrodes themselves, in the analogue amplifier.

The gain adjustment may be performed continuously, for example, every 10 ms. The main errors to be corrected by calibration are the component gain error of active electrodes and the skin-electrode impedance mismatch. The gain error is a static error, which can be calibrated once. However, the skin-electrode impedance mismatch is a dynamic error, which varies rapidly over time. A movement of the patient can thus result in a significant variation of the effective gain of the system. Thus, the calibration should be faster than these variations.

Figure 3:
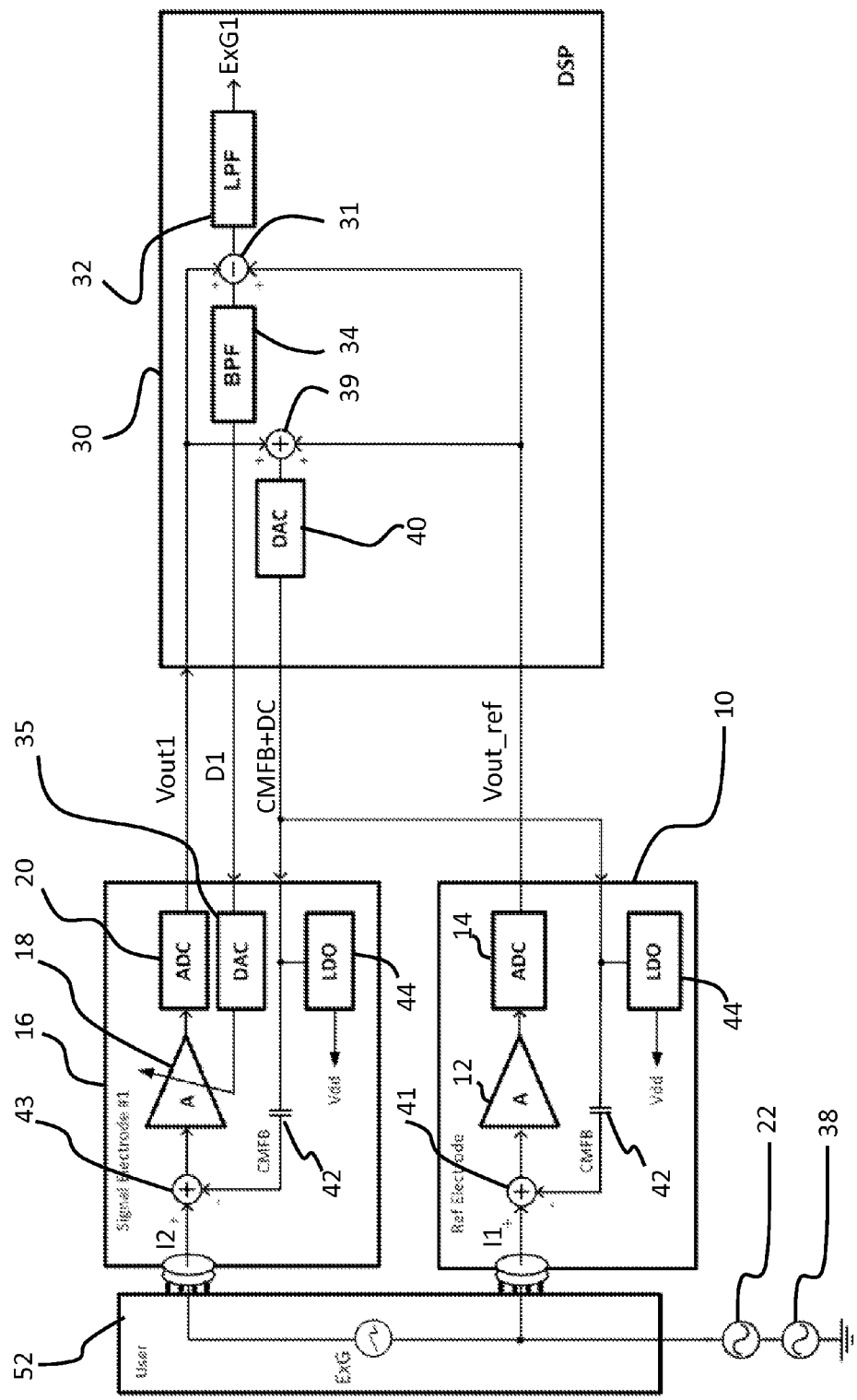
FIG. 3 shows a second embodiment of a signal acquisition system according to the disclosure.

FIG. 3 shows a second example in which a common mode feedback system is provided in addition to the CMRR gain adjustment. Again, the same reference numbers are used as in FIGS. 1 and 2 for the same or similar components.

The digital outputs from the two active electrodes are added by adder 39 in order to derive a common mode signal. By definition, the input signals comprise a common mode component and opposite differential components (VCM+0.5 VDM and VCM −0.5 VDM) so their summation provides 2 VCM (double the common mode component).

This common mode component is converted to an analogue signal by digital to analogue converter 40. This may include an attenuation or amplification corresponding to the amplifier gain A. This attenuation or amplification can be variable and controlled by the system. The end result is that the output signals Vout1, Vout-ref are essentially averaged in order to derive the common mode signal. Thus, the adder 39 and DAC 40 with its gain can together be considered to comprise averaging means.

Note that any noise generated by the DAC 40 is common-mode noise, which does not contribute to extra noise between the two active electrodes.

The common mode feedback signal is aimed at reducing the mains interference. The common mode feedback signal (CMFB+DC) output by the converter 40 comprises the extracted common mode signal for the active electrodes (CMFB) superimposed on a DC voltage. This independent DC voltage source is not shown in the figure. The DAC 40 is for example associated with a capacitively coupled amplifier that adds the common mode feedback signal to the DC voltage level. This DC voltage level may be used as the power source for the active electrodes as explained below.

This is fed back to the active electrodes through a blocking capacitor 42 and a subtractor (shown as an adder with negative input for the feedback path). The adder is shown as 41 for the reference active electrode and 43 for the signal active electrode. In this way, the AC component is subtracted from the inputs. The common mode feedback signal CMFB is thus subtracted from the two electrode signals I1 (for the reference active electrode 10) and I2 (for the signal active electrode 16).

The common mode signal extraction is performed in the signal processor 30. The system reduces the effective input common mode signal, which allows a large common mode test signal to be applied to the active electrodes without saturation.

FIG. 3 also shows a voltage regulator 44 (low drop out "LDO" voltage regulator, for example) in each active electrode. The regulator 44 regulates the combined DC and CMFB signal (e.g., before the DC blocking capacitor) into a constant DC voltage (Vdd), which is used as supply voltage for the active electrodes. For this purpose, the DC voltage level should be slightly higher than the targeted supply voltage of the active electrode. This arrangement means that the common mode feedback system can be implemented without requiring additional connections to the active electrodes; the power supply signal can be shared with the common mode feedback signal.

The LDO in the active electrodes is an optional feature. With the LDOs removed, a separate voltage supply can be used for the active electrodes, and the DC level of the feedback signal may not be important.

The common-mode feedback scheme in combination with the CMRR calibration of FIG. 2 achieves a very high common-mode rejection ratio (CMRR) for active electrode based biopotential signal acquisition systems.

The feedback scheme not only improves the CMRR of the active electrode pair, but also enables the gain trimming of active electrodes between two high-gain active electrodes. When combining the two approaches as in the circuit of FIG. 3, the system can achieve a very high CMRR, for example, 100 dB.

The common mode feedback system does not require additional connections to the active electrodes, because the feedback signal can be combined with the power supply signal.

Moreover, the skin-electrode impedance does not affect the stability of the system.

As outlined above, the test signal can be superimposed onto a DC bias voltage and then applied to a passive electrode. This arrangement is shown in more detail in FIG. 4, in which the passive electrode ("bias electrode") is shown as 50. The patient is represented by the region 52.

Figure 4:
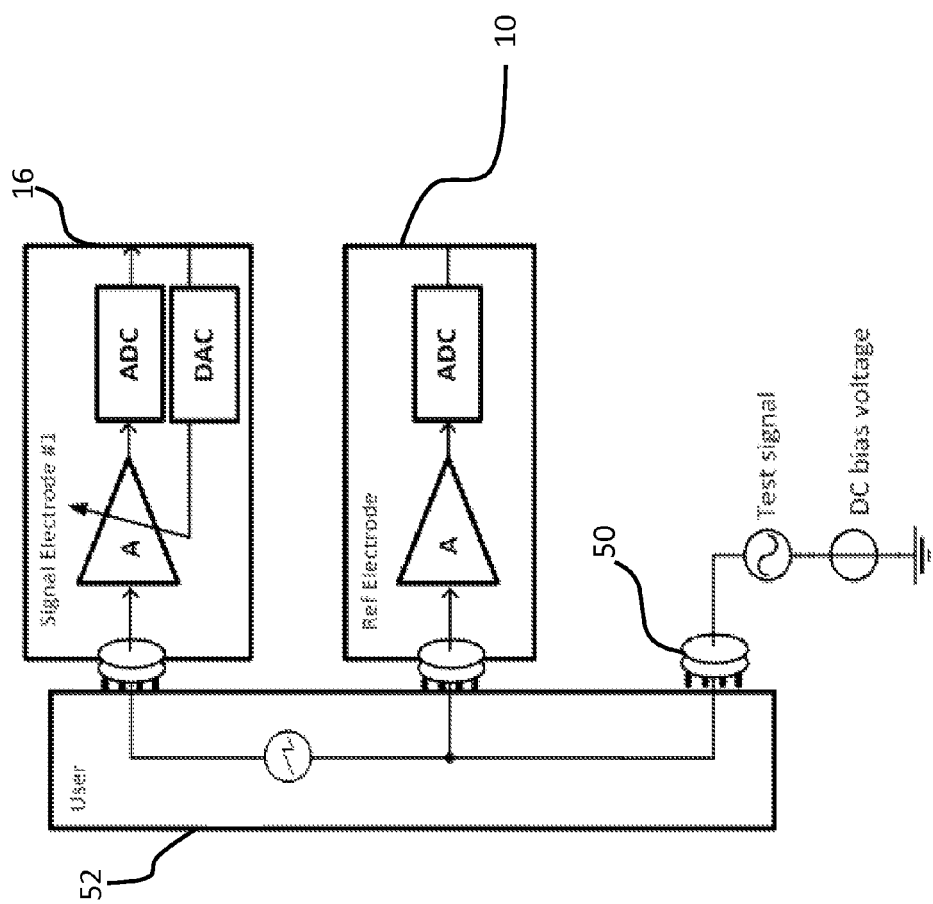
FIG. 4 shows a first way of applying the test signal.

In FIG. 4, the electrodes have resistive skin-electrode contact, and the test signal and DC biasing are provided by the bias electrode.

Figure 5:
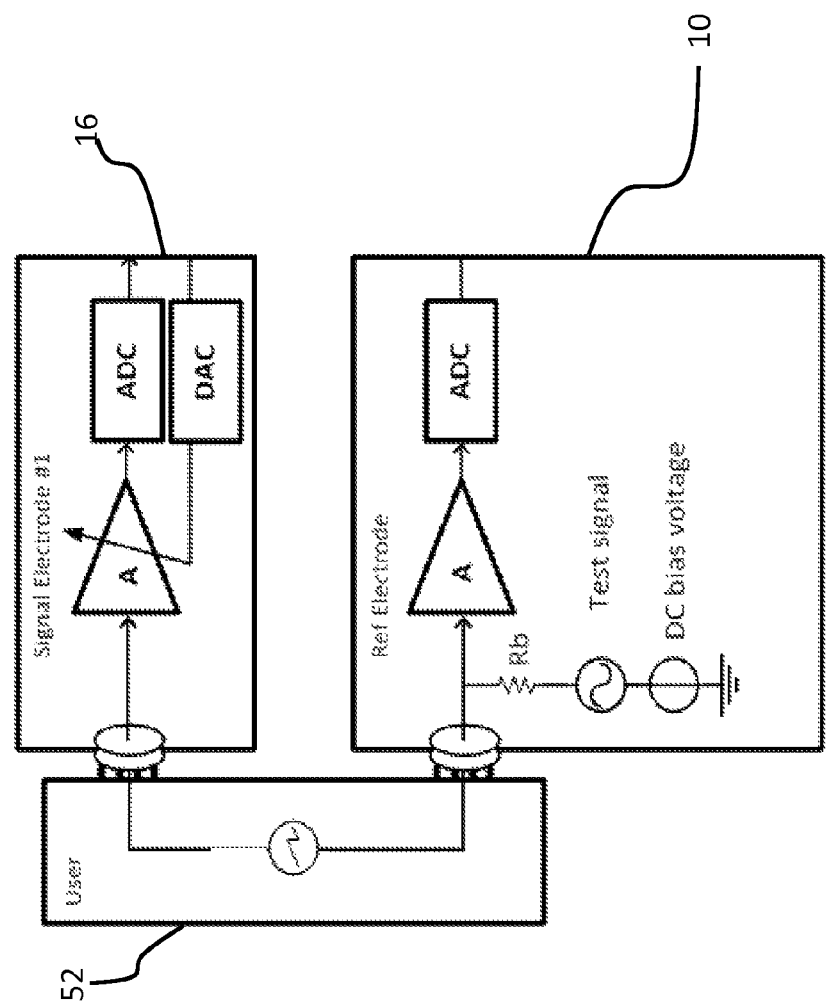
FIG. 5 shows a second way of applying the test signal.

FIG. 5 shows a first alternative, again for resistive skin-electrode contact, in which the test signal and DC bias are connected to the input of the amplifier of the reference active electrode 10 through a large resistor Rb.

Figure 6:
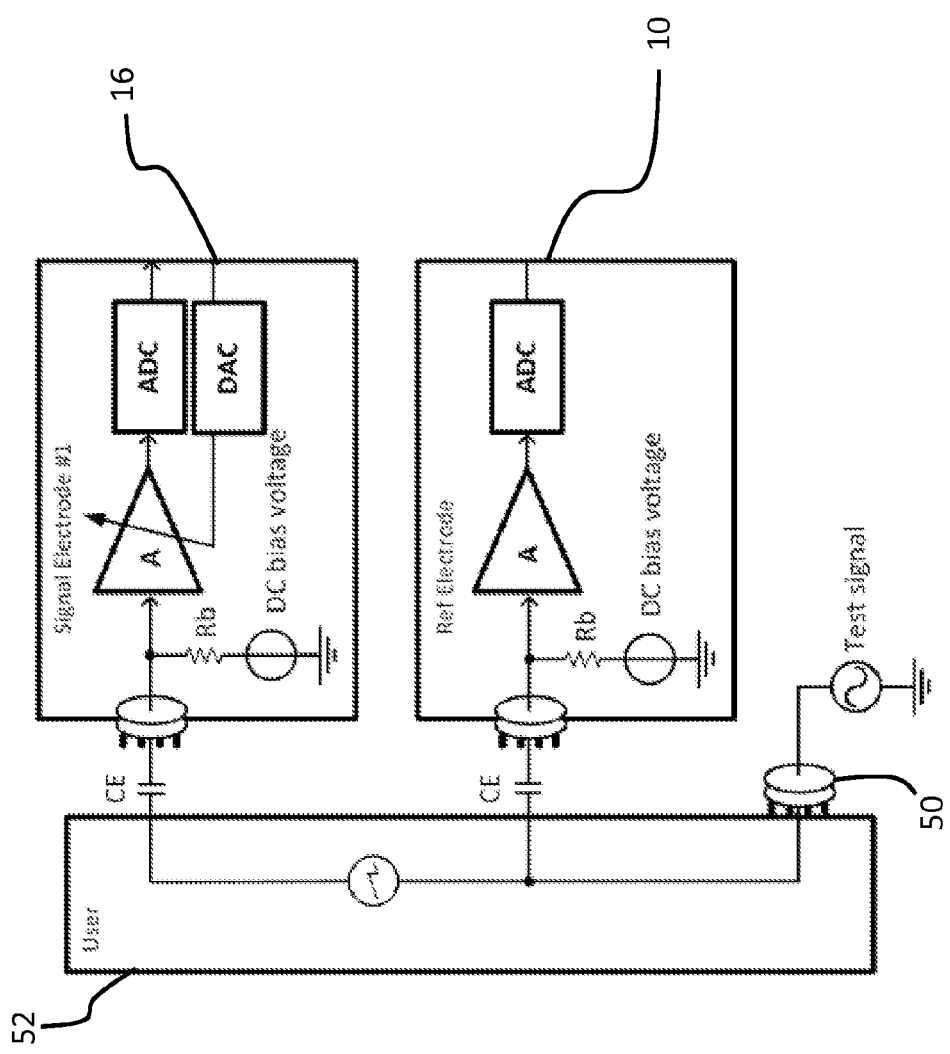
FIG. 6 shows a third way of applying the test signal.

FIG. 6 shows a second alternative, for capacitive skin-electrode contact, in which DC bias is provided to the input of the amplifier of the reference active electrode 10 through a large resistor Rb. The test signal is provided to the user through the bias electrode 50.

Figure 7:
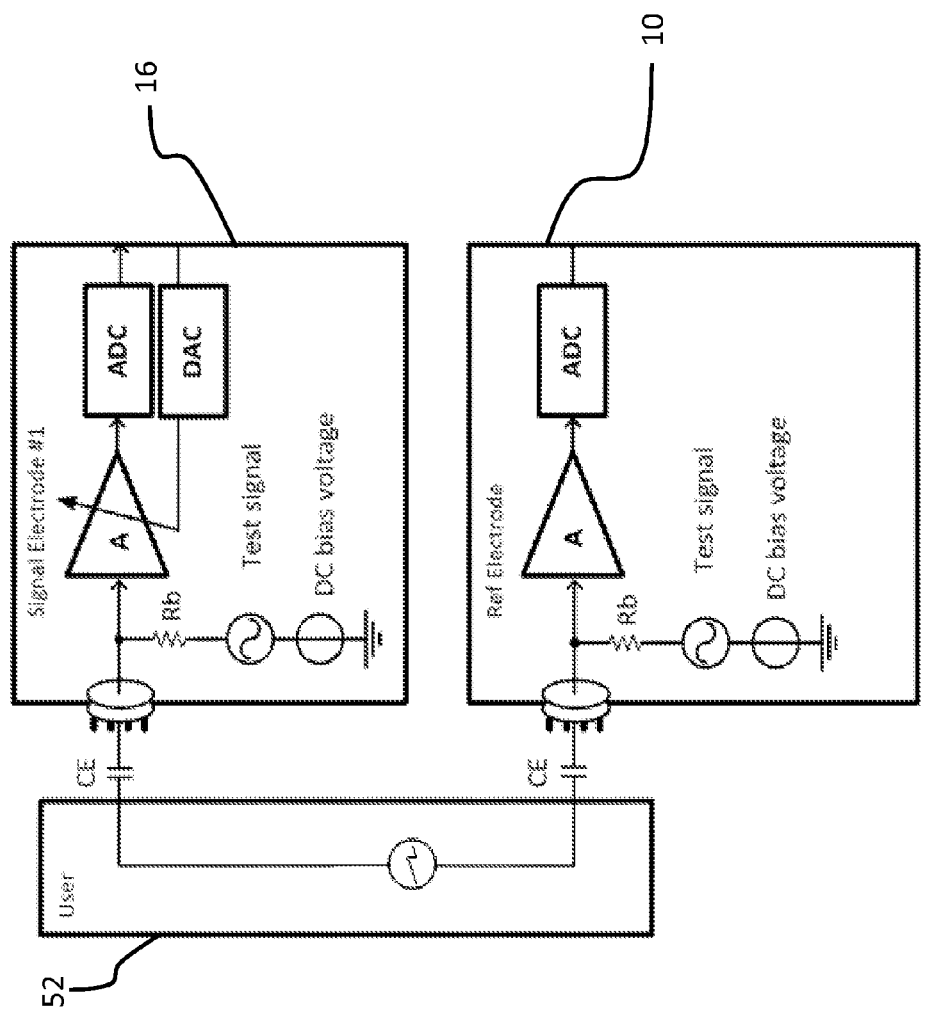
FIG. 7 shows a fourth way of applying the test signal.

FIG. 7 shows a third alternative, again for capacitive skin-electrode contact, in which DC bias and test signal are connected to the inputs of the amplifiers of all of the active electrodes through large resistors Rb.

The examples above show that the test signal can be applied to the patient through a bias electrode or it can be applied to the amplifier circuitry of one or both of the active electrodes. In either case, the test signal is coupled to one or both active electrodes. Thus, the term "coupled" should be understood as including providing the test signal to the active electrodes through the patient, or else providing the test signal to the circuitry of one or both of the active electrodes. The test signal can be superimposed on the DC bias, or else the DC bias and the test signal can be applied separately.

Figure 8:
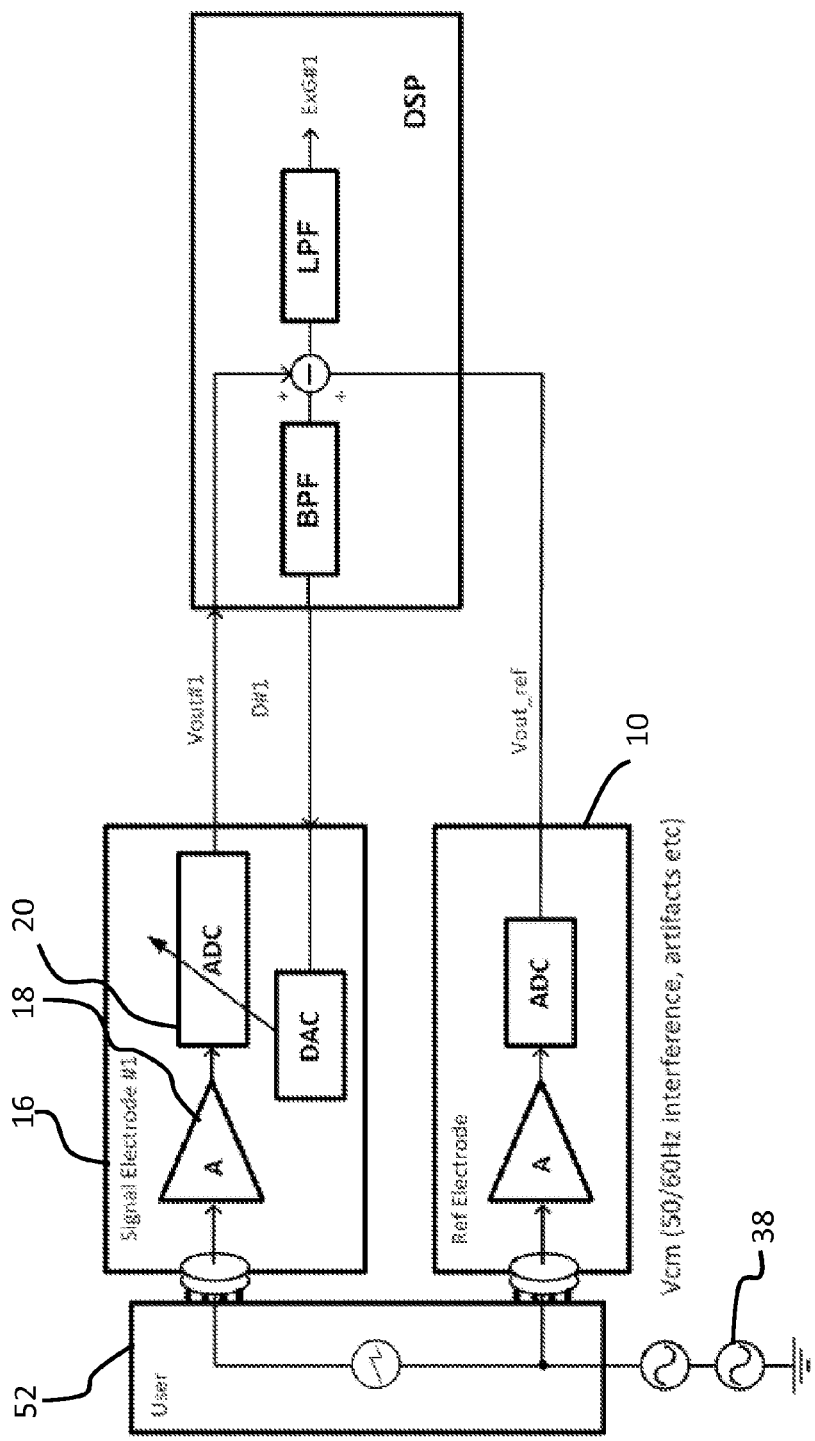
FIG. 8 shows a third embodiment of a signal acquisition system according to the disclosure.

FIG. 8 shows a variation to the circuit of FIG. 2, in which the feedback is used to control a gain of the ADC 20 of the signal active electrode instead of controlling the gain of the amplifier 18. Thus, the amplifier can have fixed gain, and the required variable gain is implemented by the ADC. The operation is as described above.

The examples above refer to a signal active electrode and a reference active electrode. However, more generally, a differential signal acquisition system requires first and second active electrodes. For a pair of active electrodes, only one variable gain is needed, and for the purposes of explanation the active electrode with variable gain is termed a signal active electrode above. This does not exclude both active electrodes having variable gain. Furthermore, in a system with N active electrodes, N−1 can have variable gain as mentioned above, but equally they may all have variable gain. In this way, all the active electrodes can be identical, and all gains can be adjusted to an overall average value for example.

By way of example, FIG. 9 shows a system with a single reference active electrode 10 and multiple signal active electrodes 16a, 16b, . . . 16N. Each signal active electrode may take the same form as shown in FIG. 2, for example, and the reference active electrode 10 may also takes the same form as shown in FIG. 2, for example. Thus, this biopotential signal acquisition system further comprises at least a third active electrode 16b comprising an integrated pre-amplifier 18b, an analogue to digital converter 20b, and digital to analogue converter 35b. Each signal active electrode has a respective output Vout1, Vout2, . . . ,VoutN and receives a respective digital gain control signal D1, D2, . . . , DN. The third (and other) signal active electrode has variable gain and is also coupled to the test signal 38.

For each signal active electrode, the digital signal processor 30 processes the digital outputs of the signal active electrode and the reference active electrode to derive the gain control signal based on a difference between the electrode outputs and the reference active electrode at the test frequency. For example, for the third signal active electrode, the subtractor 31b derives the difference between the reference active electrode output Vout_ref and the signal active electrode output Vout2, and after filtering with filter 34b derives the gain control signal D2, which is applied to the third active electrode 16b.

Each additional signal active electrode may operate in the same way, and as shown, a set of outputs ExG1, ExG2, . . . , ExGN is provided.

FIG. 9 thus represents an extension of the system of FIG. 2 to include multiple signal active electrodes.

Figure 10:
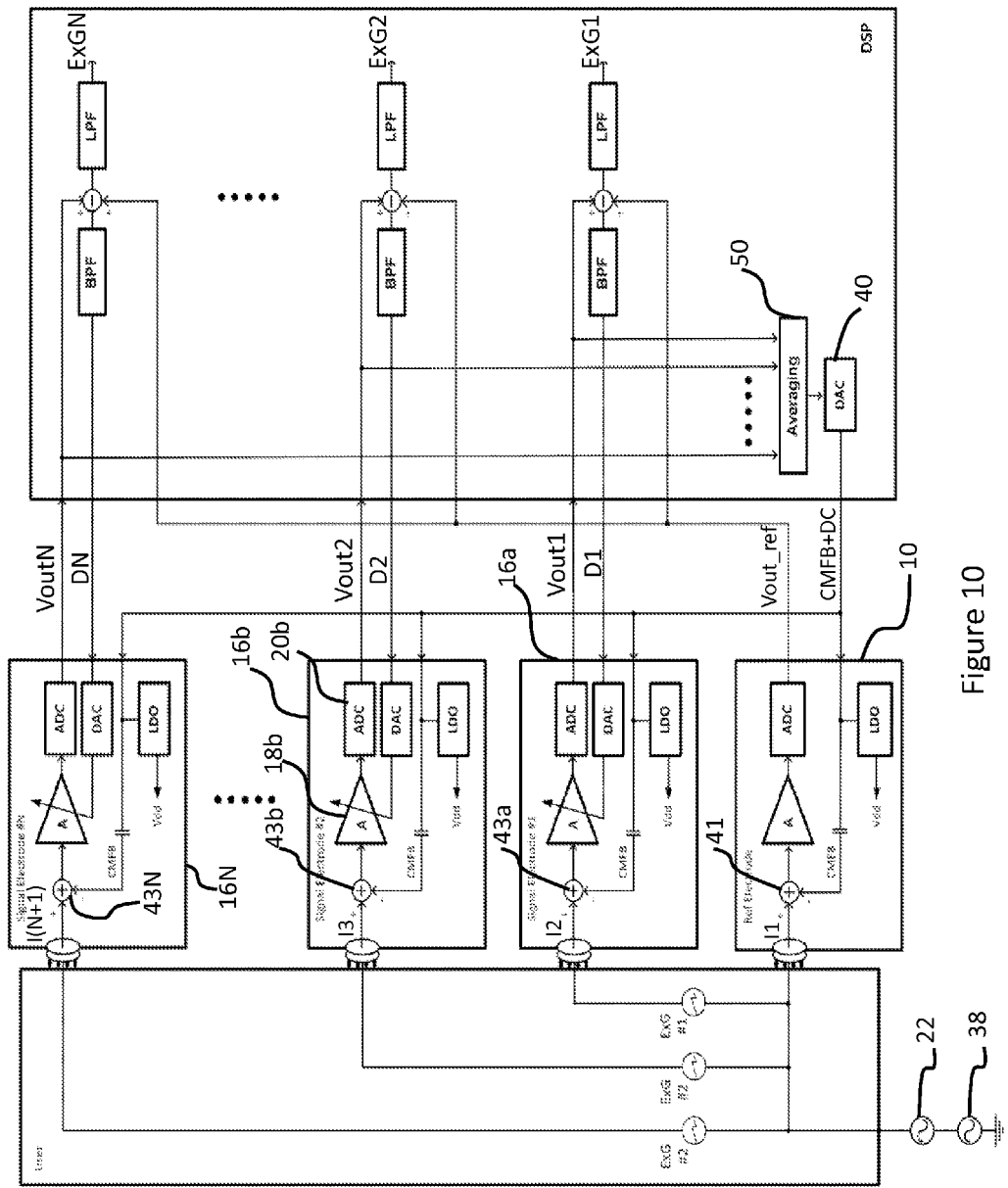
FIG. 10 shows how the system of FIG. 3 can be extended to have more than two active electrodes.

FIG. 10 shows an extension of the system of FIG. 3 to include multiple signal active electrodes.

The multiple signal active electrode are again shown as 16a, 16b, . . . , 16N, each of which takes the form as shown in FIG. 3. They each have a respective output Vout1, Vout2, . . . , VoutN, and the feeback control is based on the difference between the respective output D1, D2, . . . DN and the reference active electrode output Vout_ref. As in the example of FIG. 9, a set of outputs ExG1, ExG2, . . . , ExGN is provided.

The same common mode feedback signal CMFB+DC is used by the reference active electrode and each of the signal active electrodes. To derive this common mode feedback signal, an averaging means 50 (which can be simply implemented as part of the digital signal processing) averages the outputs of the set of signal active electrodes (Vout1, Vout2, . . . , VoutN) to derive a digital signal representing a common mode signal. The averaging means may also average the reference active electrode signal (as in the example of FIG. 3, but with multiple active signal electrodes, the average can be taken only of the active signal electrode signals). As in FIG. 3, a digital to analogue converter 40 converts the derived digital common mode signal into an analogue common mode feedback signal (CMFB+DC) which is provided to each active electrode (reference and signal) and each active electrode has a subtractor for subtracting an AC part of the common mode feedback signal (CMFB+DC) from the input signal (I1 to IN+1) to the respective active electrode. The reference active electrode subtractor is shown as 41 (as in FIG. 3), and the signal active electrode subtractors are shown as 43a, 43b, . . . , 43N.

Various other modifications will be apparent to those skilled in the art.

The invention claimed is:

1. A biopotential signal acquisition system, comprising:
a first active electrode including an integrated pre-amplifier and an analogue to digital converter;
a second active electrode including an integrated pre-amplifier and an analogue to digital converter, wherein the second active electrode has a variable gain;
a test signal generator configured to generate a test signal at a test frequency and to couple the test signal to the first and/or second active electrodes; and
a digital signal processor configured to process the digital outputs of the first and second active electrodes to derive a gain control signal based on a difference between the first and second active electrode outputs at the test frequency, and to apply the gain control signal to the second active electrode.

2. The biopotential signal acquisition system according to claim 1, wherein the gain control signal is digital, and the second active electrode comprises a digital to analogue converter.

3. The biopotential signal acquisition system according to claim 1, wherein the digital signal processor comprises a digital band pass filter tuned to the test frequency for producing the gain control signal.

4. The biopotential signal acquisition system according to claim 1, wherein the digital signal processor comprises a digital low pass filter for removing the test signal frequency before providing a system output.

5. The biopotential signal acquisition system according to claim 1, wherein the biopotential signal acquisition system further comprises at least a third active electrode including an integrated pre-amplifier and an analogue to digital converter, wherein the third active electrode has variable gain and is coupled to the test signal;
and wherein the digital signal processor is further configured to process the digital outputs of the first and third active electrodes to derive a gain control signal based on a difference between the first and third active electrode outputs at the test frequency, and to apply the gain control signal to the third active electrode.

6. The biopotential signal acquisition system according to claim 1, further comprising averaging means for averaging the outputs of the first and second active electrodes to derive a digital signal representing a common mode signal.

7. The biopotential signal acquisition system according to claim 5, further comprising averaging means for averaging the outputs of the second and third and any additional electrodes to derive a digital signal representing a common mode signal.

8. The biopotential signal acquisition system according to claim 6, further comprising a digital to analogue converter for converting the derived digital common mode signal into an analogue common mode feedback signal that is provided to the active electrodes.

9. The biopotential signal acquisition system according to claim 7, further comprising a digital to analogue converter for converting the derived digital common mode signal into an analogue common mode feedback signal that is provided to the active electrodes.

10. The biopotential signal acquisition system according to claim 7, wherein each active electrode comprises subtraction means for subtracting an AC part of the common mode feedback signal from the input signal to the respective active electrode.

11. An electronic circuit or device comprising a biopotential signal acquisition system as recited in claim 1.

12. A biopotential signal acquisition method, comprising:
capturing a first biopotential signal using a first active electrode comprising an integrated pre-amplifier and an analogue to digital converter;
capturing a second biopotential signal using a second active electrode comprising an integrated pre-amplifier and an analogue to digital converter, wherein the second active electrode has a variable gain;
generating a test signal at a test frequency and coupling the test signal to the first and/or second active electrodes; and
processing the digital outputs of the first and second active electrodes to derive a gain control signal based on a difference between the first and second active electrode outputs at the test frequency, and applying the gain control signal to the second active electrode.

13. The biopotential signal acquisition method according to claim 12, wherein the gain control signal is digital, and the method further includes, in the second active electrode, converting the gain control signal to an analogue signal and using this gain control signal to set the gain of the pre-amplifier of the second active electrode.

14. The biopotential signal acquisition method according to claim 12, wherein the method further comprises:
capturing at least a third biopotential signal using a third active electrode comprising an integrated pre-amplifier and an analogue to digital converter, wherein the second active electrode has a variable gain;
further coupling the test signal to the third active electrode; and
further processing the digital outputs of the first and third active electrodes to derive a gain control signal based on a difference between the first and third active electrode outputs at the test frequency, and further applying the gain control signal to the third active electrode.

15. The biopotential signal acquisition method according to claim 12, further comprising averaging the outputs of the first and second active electrodes to derive a digital signal representing a common mode signal, converting the derived digital common mode signal into an analogue common mode feedback signal and providing the analogue common mode feedback signal to the first and second active electrodes.

16. The biopotential signal acquisition method according to claim 14, wherein the method further comprises averaging the outputs of the second, third, and any additional active electrodes to derive a digital signal representing a common mode signal, converting the derived digital common mode signal into an analogue common mode feedback signal and providing the analogue common mode feedback signal to each active electrode.

* * * * *